(12) United States Patent
Shetterly et al.

(10) Patent No.: US 8,049,879 B2
(45) Date of Patent: Nov. 1, 2011

(54) METHOD AND APPARATUS FOR MEASURING TRANSMITTED OPTICAL DISTORTION IN GLASS SHEETS

(75) Inventors: Donivan M. Shetterly, Bowling Green, OH (US); Jason C. Addington, Sylvania, OH (US); Michael J. Vild, Toledo, OH (US)

(73) Assignee: Glasstech, Inc., Perrysburg, OH (US)

( * ) Notice: Subject to any disclaimer, the term of this patent is extended or adjusted under 35 U.S.C. 154(b) by 326 days.

(21) Appl. No.: 12/386,098

(22) Filed: Apr. 14, 2009

(65) Prior Publication Data

US 2009/0282871 A1    Nov. 19, 2009

Related U.S. Application Data

(60) Provisional application No. 61/124,178, filed on Apr. 15, 2008.

(51) Int. Cl.
*G01N 21/00* (2006.01)
(52) U.S. Cl. .................................................. 356/239.2
(58) Field of Classification Search ........................ None
See application file for complete search history.

(56) References Cited

U.S. PATENT DOCUMENTS

| | | | | |
|---|---|---|---|---|
| 5,471,297 A | * | 11/1995 | Tani | 356/239.1 |
| 5,691,811 A | | 11/1997 | Kihira | |
| 6,208,412 B1 | * | 3/2001 | Ladewski | 356/239.1 |
| 7,345,698 B2 | | 3/2008 | Abbott et al. | |
| 2004/0057046 A1 | * | 3/2004 | Abbott et al. | 356/239.1 |

* cited by examiner

*Primary Examiner* — Tu Nguyen
(74) *Attorney, Agent, or Firm* — Brooks Kushman P.C.

(57) ABSTRACT

An apparatus and associated method for measuring transmitted optical distortion in a glass sheet includes a glass stand which receives a glass sheet for mounting between a background screen which includes a matrix of spaced apart dots, and a digital camera which captures (1) an image of the glass sheet surface, and (2) an image of the dot matrix transmitted through the glass sheet. The captured images are downloaded to a computer that is suitably programmed to analyze the image data to (1) determine the presence of any markings or elements on the surface of the glass sheet that should be isolated from the dot matrix image, (2) modify the background image to eliminate the image data corresponding to any such surface markings or elements from the image, and (3) determine characteristics indicative of optical distortion in the modified image of the dot matrix background transmitted through the glass sheet.

2 Claims, 7 Drawing Sheets

METHOD AND APPARATUS FOR MEASURING TRANSMITTED OPTICAL DISTORTION IN GLASS SHEETS

CROSS-REFERENCE TO RELATED APPLICATIONS

This application claims the benefit of U.S. provisional application Ser. No. 61/124,178 filed Apr. 15, 2008, which is hereby incorporated herein by reference.

BACKGROUND OF THE INVENTION

1. Field of the Invention

This invention relates to a method and apparatus for measuring transmitted optical distortion in glass sheets.

2. Background Art

Manufacturers of glass sheets, particularly glass sheets formed into various curved shapes for use as automotive windshields and backlites, are interested in measuring and evaluating the amount of optical distortion in the formed sheets that might be perceived by a human observer, such as the operator or passenger in a vehicle in which the glass may be mounted as the windshield or backlite. One of the problems associated with evaluating the glass sheets is that surface markings or elements, such as the metal heating/defrosting element typically affixed to backlites, may complicate or even corrupt the distortion analysis if the marking/element is not identified and isolated from the distortion analysis.

SUMMARY OF THE INVENTION

The present invention provides an apparatus and associated method for measuring transmitted optical distortion in a glass sheet, including a glass stand which receives a glass sheet for mounting between a background screen which includes a matrix of spaced apart dots, and a digital camera which captures (1) an image of the glass sheet surface ("the surface image"), and (2) an image of the dot matrix transmitted through the glass sheet ("the background image").

The system includes controllable lighting which may be activated as and when required to properly illuminate (1) the glass sheet surface whenever a surface image is desired, and (2) the dot matrix background whenever a background image is required.

The digital images are downloaded to a computer that is suitably programmed to analyze the image data to (1) determine the presence of any markings or elements on the surface of the glass sheet that should be isolated from the dot matrix image, (2) modify the background image to eliminate the image data corresponding to any such surface markings or elements from the image, and (3) determine characteristics, such as magnification and lens power, indicative of optical distortion in the modified background image of the dot matrix transmitted through the glass sheet.

Once pixels in the surface image have been identified as corresponding to surface markings or elements, the data in the corresponding location in the background image is modified to mask, or eliminate the surface marking or element from the distortion analysis.

The magnification and lens power are preferably determined for each dot of interest in the dot array in the modified background image by comparing (1) the distances between the dot of interest and its neighboring dots with (2) the known, undistorted distances between those dots.

Various statistical information can be reported for pre-defined areas of the glass sheet, including the maximum, minimum, range, mean, and standard deviation in lens power, or other indices of distortion which may be of interest.

The system and method of the present invention can take the form of a stand-alone laboratory or production floor installation, or it may be installed in-line of other processing stations utilized in glass sheet processing equipment, such as automobile windshield and backlite fabrication lines.

The system may be programmed by the user to graphically and numerically display various indicia of optical distortion, including those indicia most relevant to industry standards such as ECE R43, or other indicia considered relevant in the industry to the analysis of the optical transmission quality of formed and fabricated glass sheets. And, though the image data corresponding to the surface markings or elements (such as a heater grid) are preferably removed from the image data when the distortion analysis is conducted, surface image data can be restored and displayed graphically along with the various indicia of optical distortion to illustrate the location of any such surface elements on a depicted distortion graph for the glass sheet.

DETAILED DESCRIPTION OF THE PREFERRED EMBODIMENT(S)

Figure 1:
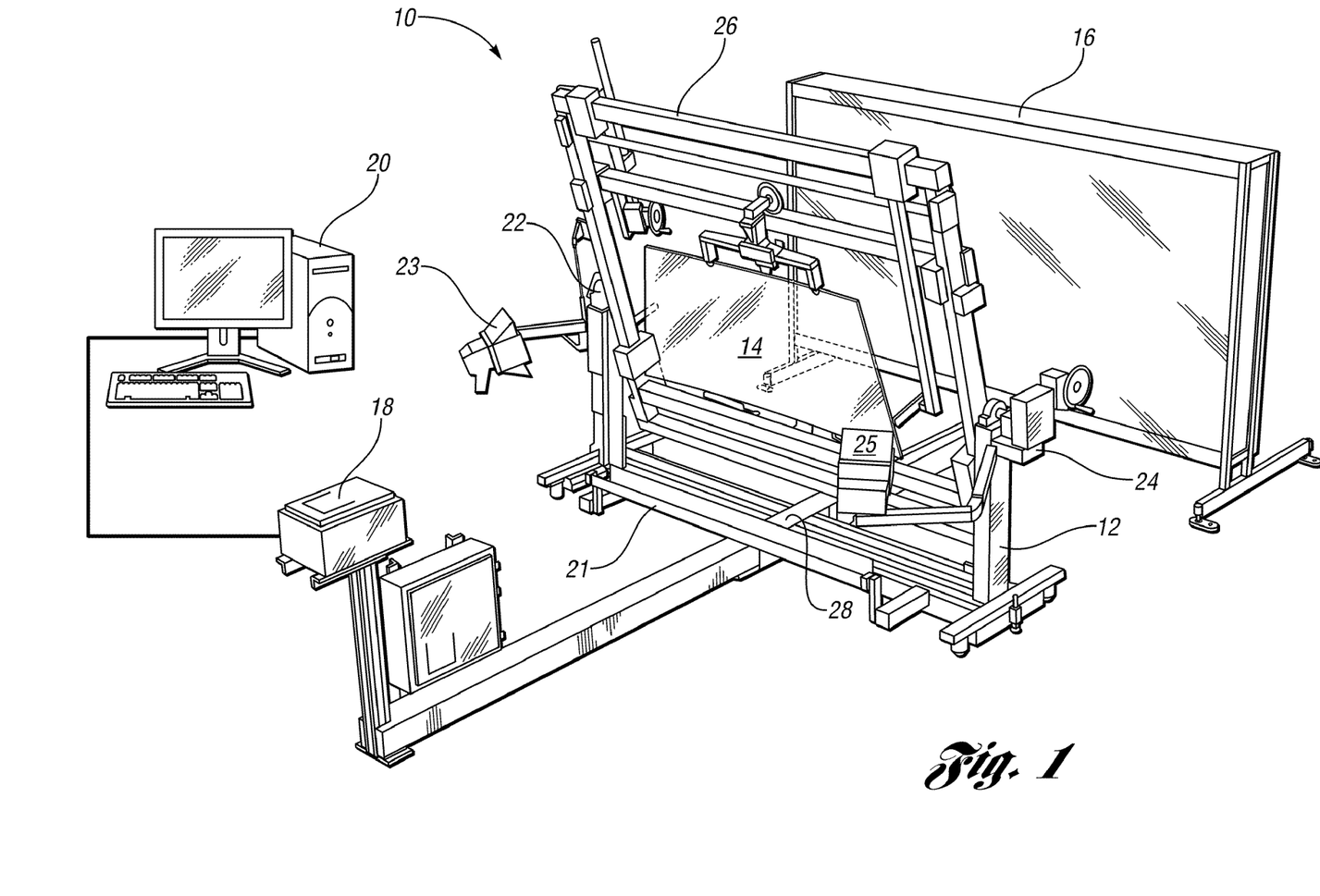
FIG. 1 is a perspective view of the apparatus of the present invention.

Referring to FIG. 1, the system 10 of the present invention includes a glass stand 12 for mounting a glass sheet 14 between a point array screen 16 and a digital camera 18. The digital camera 18 is operatively connected to a conventional computer 20 to facilitate periodic downloading of image data for processing and analysis according to the method of the present invention. In one embodiment, the glass stand includes first and second adjustment mechanisms 22 and 24 to allow for rotational adjustment of the mounting frame 26 about a generally horizontal axis, and third adjustment mechanism 28 to rotate the glass frame 26 about a generally vertical axis, in order to orient the glass sheet in the same position in which the glass would be installed in use in a vehicle. The dot array screen provides an array of dots positioned in a selected pattern and at a known predetermined distance from each other such that the background image of the dot array is projected onto the camera 18 through the glass sheet 14 mounted therebetween.

Figure 2:
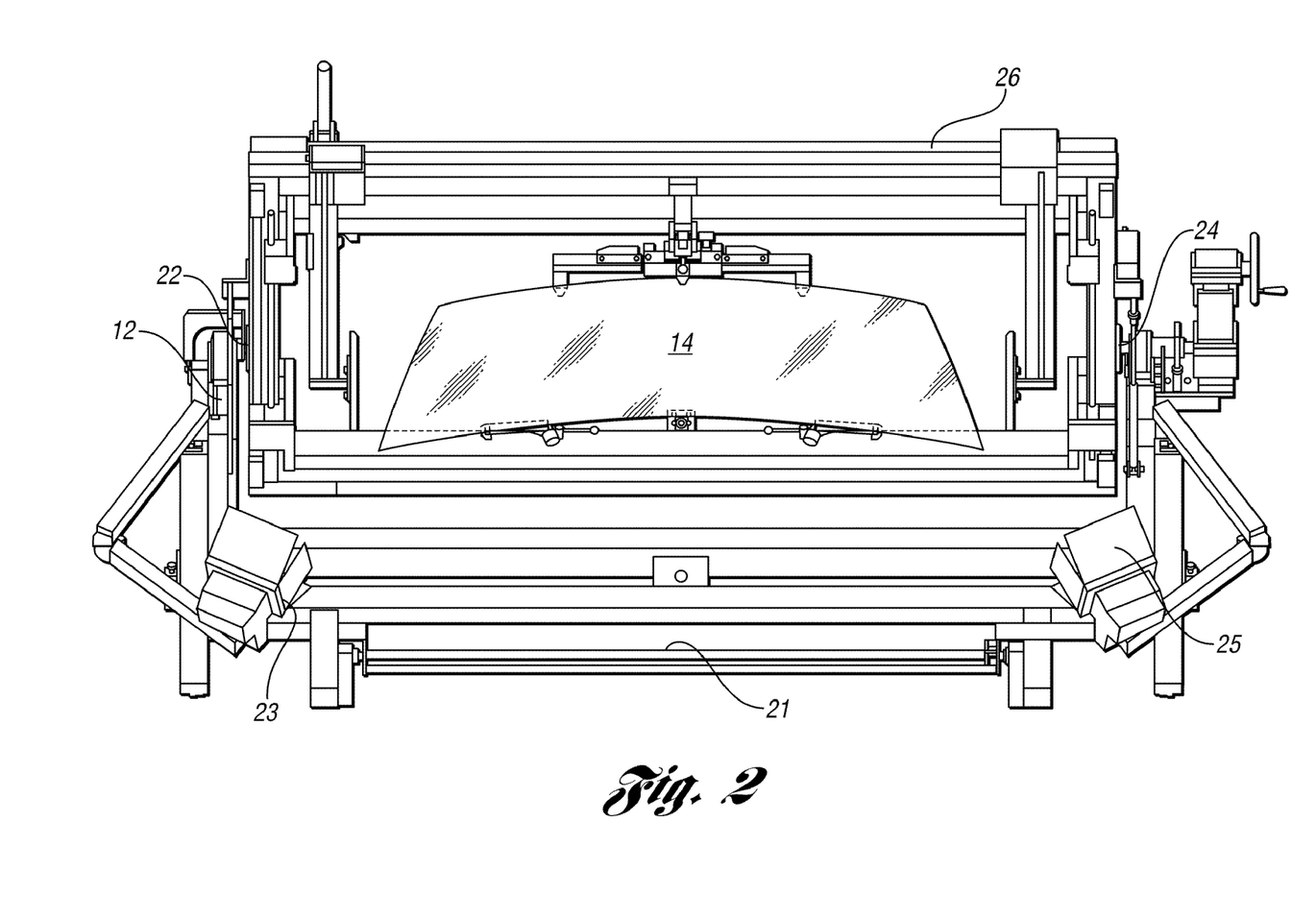
FIG. 2 is an isolate view of the glass stand including the glass sheet surface lighting used in one embodiment of the present invention.

The system 10 of the present invention also includes at least one light source mounted so as to controllably illuminate the surface of a glass sheet mounted for analysis. In the embodiment illustrated in both FIGS. 1 and 2, a first light source 21 is mounted on the stand below the glass sheet. In this embodiment, the first light source 21 is preferably a conventional fluorescent light which spans substantially the entire width of the glass sheet, to provide illumination of the surface nearest to the digital camera 18. Second and third light sources, 23 and 25 respectively, are mounted on the frame on each side, respectively, of the sheet for controllably illuminating the glass sheet surface when required, as further described herein. In the illustrated embodiment, each of the second and third light sources 23 and 25 are commercially available quartz-halogen lights.

In the illustrated embodiment, the lights are suitably connected to allow the computer to control the lighting to adequately illuminate the glass surface when a surface image is acquired, and adequately illuminate the background screen when a background image is acquired. In particular, the background screen lighting may be deactivated when a surface image is acquired, to provide a relatively dark background in contrast to the illuminated surface. Conversely, the surface lighting may be deactivated as required to insure that the background screen is properly illuminated whenever a background image is acquired. In addition, one or more of the surface lights may be activated or deactivated to insure that the acquired surface image does include a reflected image of the light source. In the illustrated embodiment of the invention, an image of the fluorescent light source 21 below the glass sheet may be reflected on the glass surface when the glass sheet is mounted at a particular angle on the stand 12. The stand may include one or more limit switches that are operably connected to the light source, such that the light source in automatically deactivated whenever the stand 12 is adjusted to mount the glass sheet at these particular angles, so that the surface illumination is then only provided by the side lights 23, 25 to insure that there is no reflected image of the light source when a surface image of the glass sheet is acquired. It will, of course, be appreciated by those skilled in the art that various light sources, arranged at various positions, may be utilized to adequately illuminate the glass sheet surface as needed without departing from the spirit of the present invention.

Figure 3:
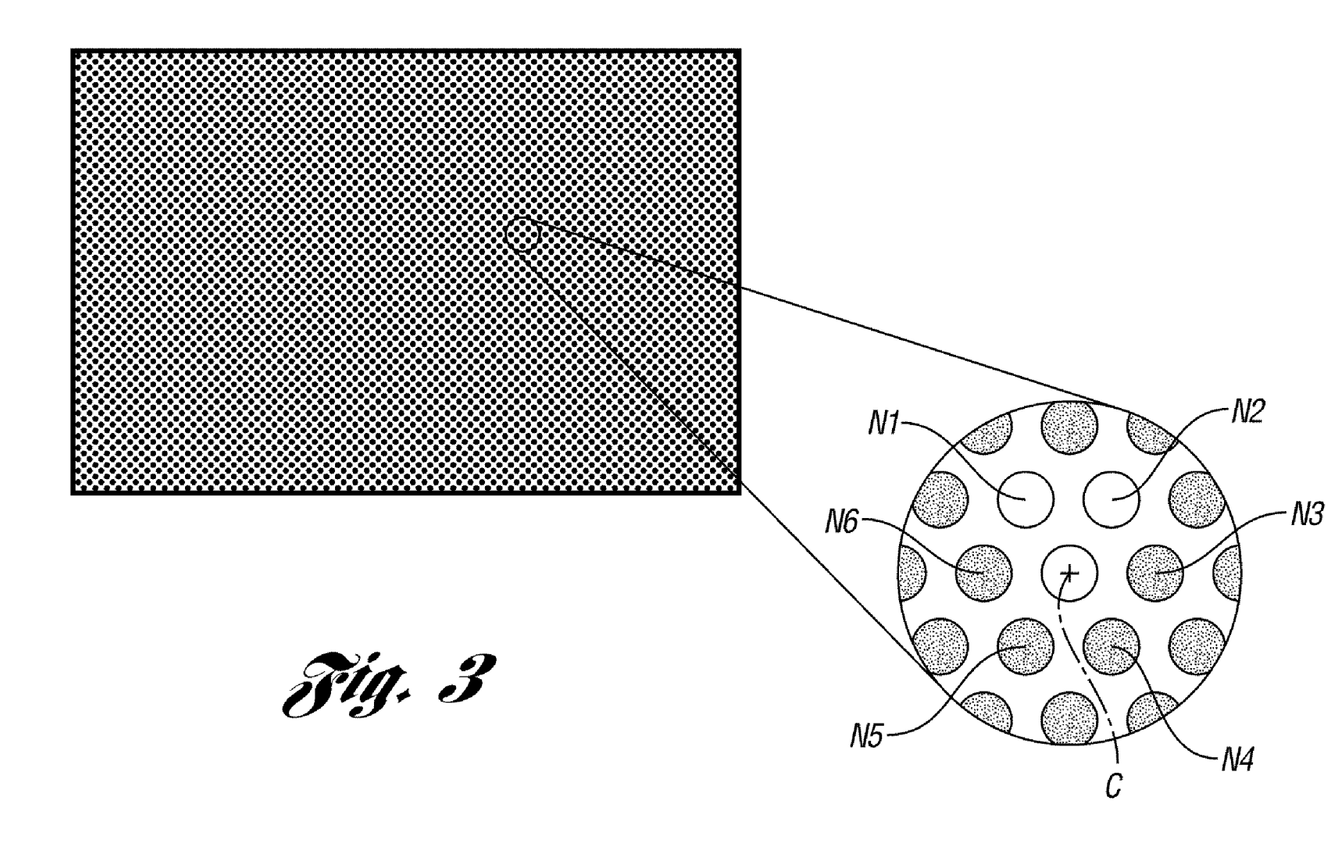
FIG. 3 is a front view of the dot array sheet used in one embodiment of the present invention.

In one embodiment of the invention, as illustrated in FIG. 3, the dots on the screen 16 are arranged such that each dot (dot of interest, C) other than boundary dots has six immediate neighboring dots, N1-N6, that are at an equal distance from the dot of interest in a hexagonal pattern. In one embodiment of the invention, the dots on the array screen are circles 3.5 millimeters in diameter, and the distance between the center of each dot and each of its six immediate neighbors is 5.5 millimeters. It will be appreciated, however that the "undistorted" dot sizes and distances utilized in the analysis are not the actual sizes and distances measured on the screen 16, but instead are the dot size and distance measured in an image focused at the distance between the camera and the mounting location of the glass sheet. It will also be appreciated that, though the dot is preferably circular in shape, other similar shapes may be employed without departing from the spirit of the present invention.

The digital camera 18 is mounted to collect images of both the illuminated surface of the glass sheet and the dot array screen 16 transmitted through the glass sheet 14 mounted on the glass stand. In one embodiment, the digital camera is a commercially available 12.8 MPa SLR-type camera. The camera 18 is connected via a conventional data line to a computer 20 which is suitably programmed to acquire the digital images of the glass sheet surface and the dot array screen from the camera, process the image data to obtain the desired resolution for the data.

The computer 20 analyzes the surface image data to determine whether there are any surface marks or elements on the glass sheet that should not be considered in the optical distortion analysis. The system then locates and isolates the data corresponding to any such surface marks or elements in the image of the matrix, then analyzes the image of the matrix, without considering the isolated data, to develop various indicia of distortion in the glass sheet according to the method of the present invention as further described herein. The computer is also programmed to present the derived image distortion information in both graphical (e.g., color-coded images) and statistical forms. The system is preferably capable of superimposing the surface marks or elements on the graphical display of the image distortion information so that, for example, a heating grid on the glass sheet surface is viewed simultaneously with the graphical distortion information for the sheet.

In one embodiment, the dot array screen is a light box that utilizes conventional lighting 27 (such as fluorescent lights, not shown) mounted in the light box behind a translucent panel upon which a contrasting dot array, preferably in the form of black dots, is printed, painted, or otherwise applied using conventional methods. The digital camera is connected to the computer using known methods, preferably so that the acquisition of the image by the camera may be controlled by the computer. The lighting in the light box is preferably controlled by the computer, so that it may be momentarily turned off, to provide a dark background, while the surface image of the glass sheet is obtained, and then turned on to illuminate the dot array background during the period when the camera is obtaining the transmitted image of the dot array screen.

The computer 20 is programmed to perform the image acquisition, modification and analysis steps described hereinafter for each glass sheet to be measured, as well as to display the resulting distortion indicia in graphical and/or numeral formats.

To mask particular zones and/or irrelevant surface anomalies, so as to eliminate data from those areas from processing or further consideration, the computer 20 deactivates the lighting 27 illuminating the background screen and activates one or more of the surface lights 21, 23 and 25 prior to controlling the camera to acquire an image of the surface of the glass sheet 14. The surface image data is then analyzed to detect the presence of surface markings and/or elements. In the embodiment illustrated in FIGS. 1 and 2, any surface markings or elements will appear in the image of the illuminated glass sheet surface as relatively light in contrast to unmarked or unadorned portions of the surface which will appear relatively dark. In one embodiment, all of the relatively lighter pixels are noted. Computer 20 subsequently restores illumination to the background screen and acquires an image of the dot matrix background screen as transmitted through the glass sheet.

Prior to performing the distortion analysis on this image data, the system eliminates the values for all of the pixels noted in the surface image as corresponding to a surface mark or element. In one embodiment, the system replaces the eliminated image data by interpolated data derived from values of neighboring pixels that have useful data (i.e., data that has not been identified to be eliminated as corresponding to surface marks or elements). In particular, a two-dimensional planar interpolation may be utilized to provide replacement data for the eliminated pixels. In this manner, surface markings or elements are effectively masked from image of the dot matrix transmitted from the background screen and eliminated from the distortion analysis. Thus, detection and masking of surface marks and elements, such as the edge of the glass sheet, paint bands, heater grid patterns, and antenna wires, and/or other attachments or fixtures, is accomplished as desired to eliminate these areas from review and consideration in the distortion analysis.

It should be appreciated by those skilled in the art that, although the surface image is analyzed in the illustrated embodiment to locate the heater grid and other elements or markings on the glass surface for the purpose of isolating them from the background image data for a more accurate distortion analysis, the surface analysis performed by the system could be adapted to identify cosmetic defects on the glass surface, such as holes in surface paint or discontinuities in the heater grid wires.

In one embodiment, the system calculates and displays lens power data associated with various predefined zones on the glass sheet. In particular, ECE R43 specifies various zones of interest on automotive windshields and backlites for which distortion data thresholds are measured and analyzed. In the table shown in FIG. 3, for example, various lens power data is provided in millidioptors for each zone, including the maximum lens power (positive magnification), minimum lens power (negative magnification), range (the difference between the identified maximum and minimum lens powers), mean lens power, and standard deviation. While ECE R43 zones are defined, the user may also define other zones of interest as desired.

Figure 4:
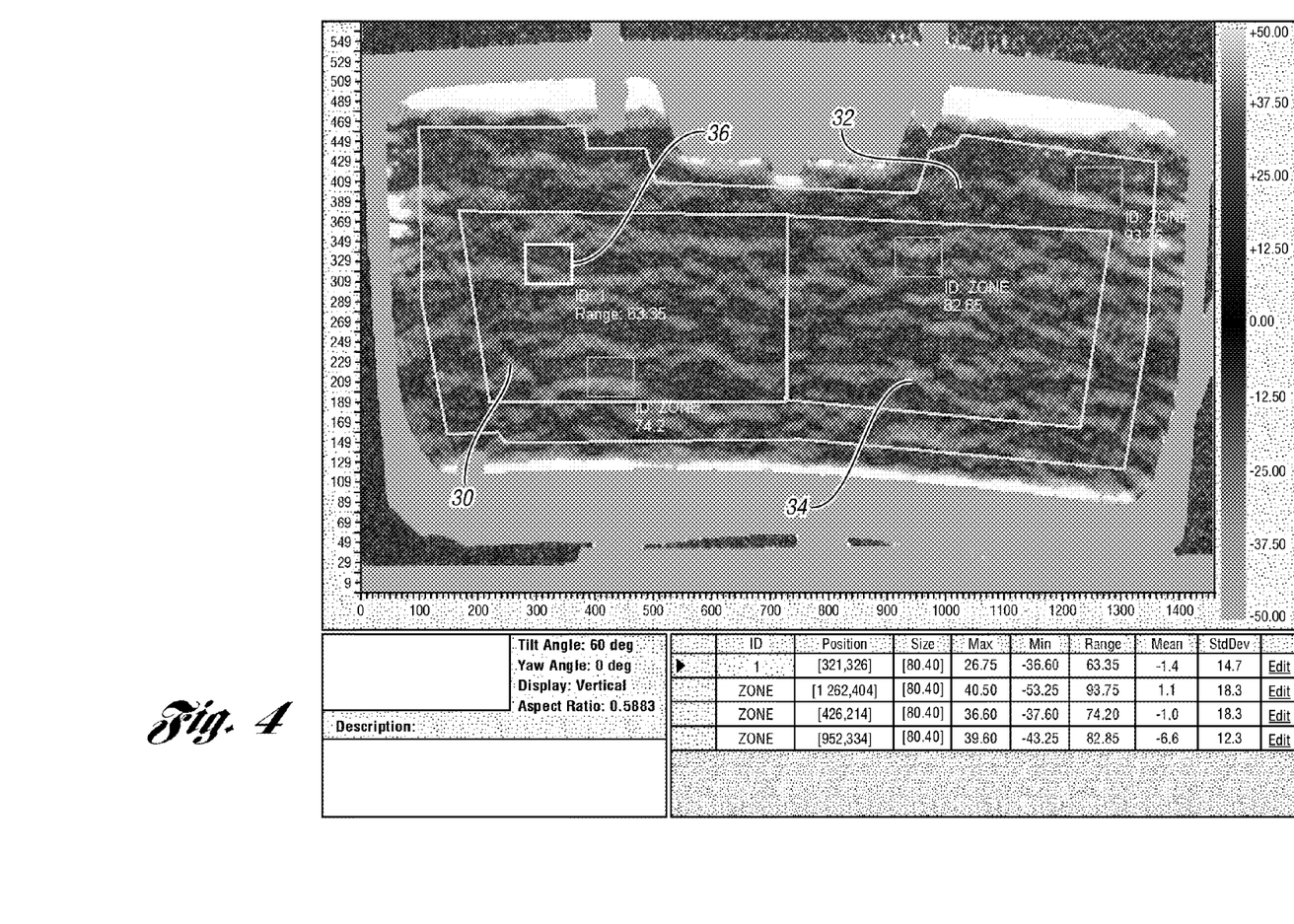
FIG. 4 is a computer display screen view of the measured results for a glass windshield measured using the apparatus and method of the present invention.
Figure 6:
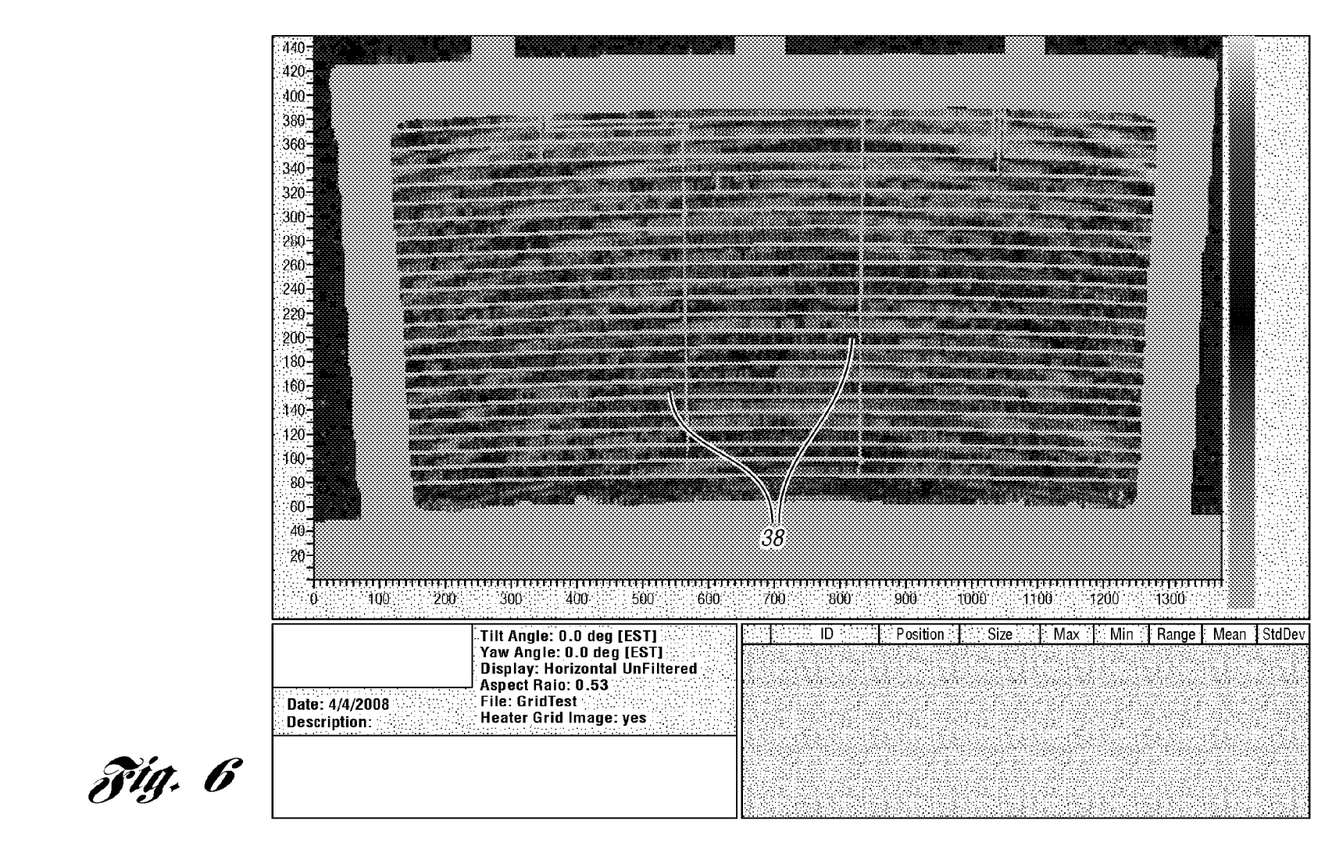
FIG. 6 is a computer display screen shot illustrating a depiction of vertical distortion measured in a glass windshield with the surface elements superimposed thereon.

One embodiment of the present invention also provides a graphical, color-coded display of the distortion using the measurement data developed for the displayed glass sheet. For example, as illustrated in FIG. 4, all areas having positive lens power are shown in red, those areas having a negative lens power are shown in green, and those areas having zero lens power (no distortion) are shown in black. As illustrated in FIG. 6, the system preferably provides the user with the option with superimposing surface image data on the graphical color-coded display so that the distortion pattern on the glass sheet can be viewed in the context of any surface elements, such as heater grids 38, antenna wires, et cetera.

According to the method of the present invention, the digital image data of the background matrix acquired from the camera 18 is resolved, or filtered, to eliminate noise, reduce resolution of the image to that approximating how the image would be perceived by a human viewer, and/or otherwise reduce the amount of image data as desired to eliminate unnecessary processing time. Various known filtering techniques, such as data averaging, may be employed to resolve the data. In one embodiment, two standard filters are developed to provide data which has been empirically shown to correlate with the "4-5-6" and "4-5-12" filters used on another optical distortion measuring system currently available from ISRA Surface Vision GmbH, so as to allow industry users to develop comparable distortion indicia for their products regardless of which measuring system is used.

The resolved image data is then processed to locate the center of each of the dots in the image. Once the centers are located, a magnification value is developed for each dot in the image. In one embodiment, the distance from the dot of interest (the center dot) from each of its six neighbors is calculated. The ratio of the average of those distances over the known, undistorted distance is established as the magnification for that dot. The lens power is then calculated for each dot. This value is typically expressed in millidioptors, the quantity often used in the glass industry for this measurement.

The system proceeds in a stepwise fashion to determine magnification and lens power values for each of the dots in the image. The lens power is then also preferably resolved into its vertical, horizontal, and shear components. Various statistical data is next developed for predefined regions and predefined zones in the glass sheet.

FIG. 4 illustrates a region 36 utilized in one embodiment of the invention. The size and shape of the region 36 may be defined by the user depending upon the desired precision and amount of derived information, and/or processing constraints. In one embodiment, a region size of 40 millimeters by 80 millimeters is used. The region is moved in a stepwise fashion through the zone so that each point in the zone is included in at least one of the region processing steps. At each step, each point in the region is accessed to determine the maximum lens power and the minimum lens power for all the points in the region, as well as the range (the difference between the maximum lens power and the minimum lens power) for those points. At the next step, the region is moved within the zone to include one or more new points and the maximum, minimum and range are determined for all the points in the region at its new location. This process is repeated until all the points in the zone have been included in the region for at least one step of the regional processing steps. It will be appreciated that the region can be repositioned within the zone at each step by any distance, as desired by the user, so long as all the points within the zone are located within the region during at least one of the processing steps. In one embodiment, the region is moved through the zone one pixel at a time, so that each point in the zone is, for example, the topmost, leftmost point in the region at a particular processing step. Of course, processing time can be reduced by moving the region so as few points as possible are included in the region in more than one processing step. For example, if the region was suitably sized and shaped to include one quarter of the dots within a zone at each step, minimal processing time could be achieved by moving the region to a position in which it contains no dots processed in the previous step (i.e., moving the region to each of the four locations including one quarter of the dots within the zone) so that each dot is included in only one regional processing step.

In the embodiment illustrated in FIG. 4, once this stepwise regional processing has been completed for a particular zone, the relevant distortion indicia, and the location of the region within the zone, are displayed for that region which has the greatest range (i.e., the greatest difference between its maximum lens power and its minimum lens power). Thus, when a particular glass sheet is completely processed utilizing the method illustrated in FIG. 3, a single region will be identified in each of the zones of the glass sheet, with the identified regions representing the location and value of the maximum lens power range for that zone. It will be appreciated that other optical distortion indicia can be calculated, identified, and displayed by region and/or for each zone, as desired by the user.

Referring again to FIG. 4, various distortion indicia are developed for predefined zones 30-34. In one embodiment of the system, the image distortion value associated with each point is the lens power in millidioptors, and the distortion indicia includes the maximum lens power, the minimum lens power, the range (i.e., maximum minus minimum lens power) the mean, and the standard deviation for each ECE R43 zone on the glass sheet thereby providing the analysis and data used to measure the optical quality of glass according to current defacto international standards. Of course, it will be appreciated that other distortion and indicia may be developed using the techniques of the present invention. Similarly, other zones of interest may be defined on the glass sheet as desired, depending upon industry standards, design concerns, and/or the nature of the use of the glass sheet.

Figure 5:
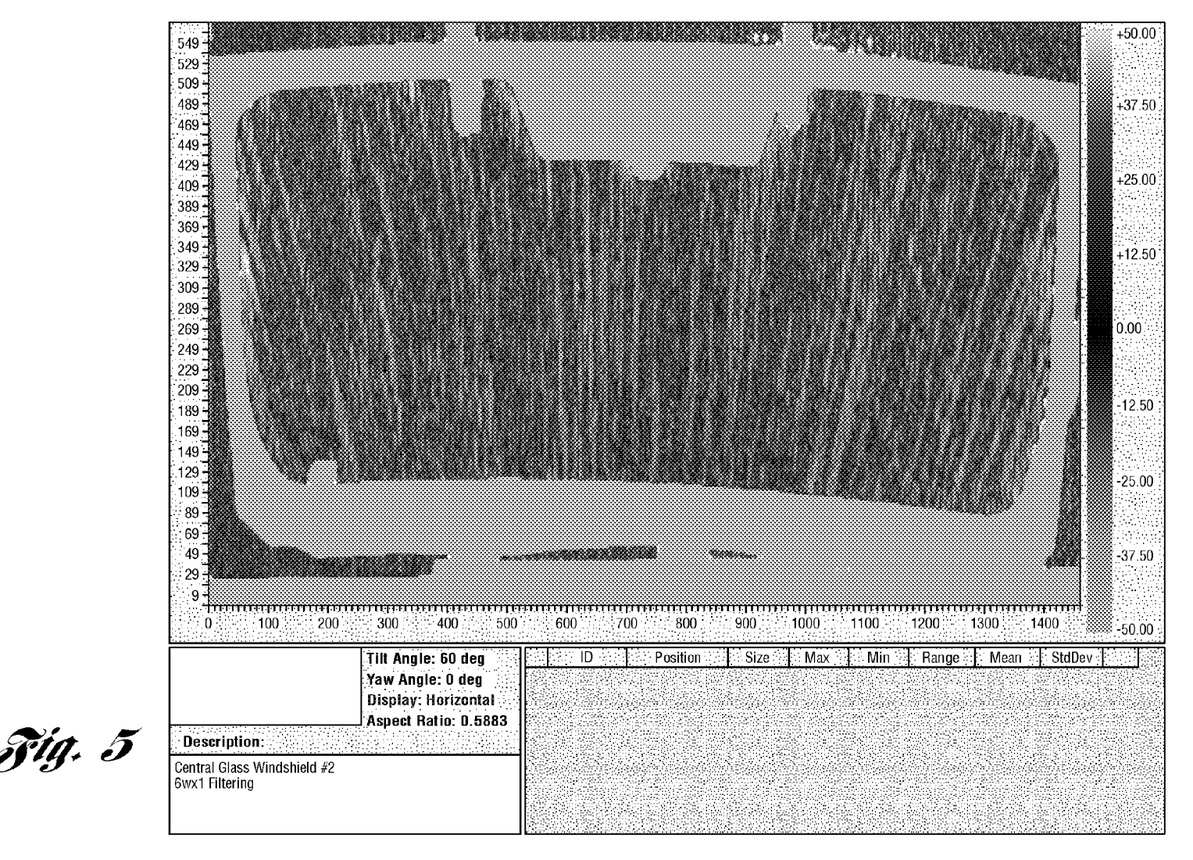
FIG. 5 is a computer display screen shot illustrating a depiction of vertical distortion measured in a glass windshield.

As illustrated in FIGS. 4 and 5, data and graphical displays relating only to horizontal distortion, or only to vertical distortion, can be similarly provided for each glass sheet. It should be noted that the distortion often characterized by those in the art as "horizontal" distortion, illustrated in FIG. 4, is actually distortion indicia relating to the vertical component of the variation in the distances between the dots and the distorted image and an undistorted image. Similarly, the distortion often characterized by those skilled in the art as vertical (or drawline) distortion, illustrated in FIG. 5, actually depicts the horizontal component of the variance in the distance between the dots from the distorted image (viewed through the glass sheet) and an undistorted image of the dot array screen.

In the embodiment of the invention shown in FIG. 3, the system 10 is provided as a stand-alone product which may be located in an engineering laboratory or production environment. Other contemplated embodiments of the system 10 include in-line installations in glass sheet processing systems, whereby the optical distortion may be measured for each glass sheet as it is conveyed through the fabrication process.

Figure 7:
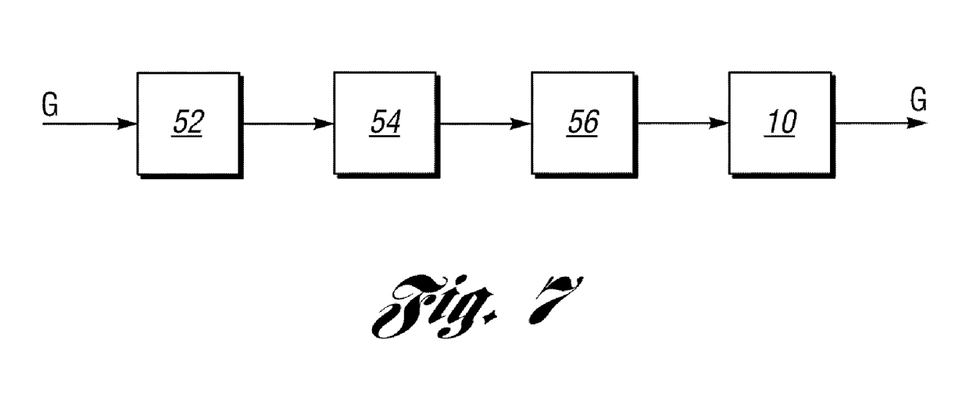
FIG. 7 is a schematic diagram of the system of the present invention installed in-line in a typical automotive backlite forming and tempering line.

For example, FIG. 7 illustrates a typical automotive backlite heating, bending, and tempering system 50 which includes the system 10 of the present invention in-line. In this installation, the glass sheets (indicated as G) enter a heating zone 52 where the glass is softened to a temperature suitable for forming the glass into the desired shape. The heated glass sheet is then conveyed to a bending station 54 where the softened sheet is formed to the desired shape, and thereafter further conveyed to a cooling station 56 where the glass sheet is cooled in a controlled manner to achieve the appropriate physical characteristics. In this embodiment, the glass sheet would then be conveyed out of the cooling station to a transport position from which the sheet is moved from the conveyor and mounted on the glass stand for image acquisition and analysis according to the present invention. Following the measurement, the glass sheet would then be removed from the stand and deposited on a conveyor, or in a storage rack, for further processing. It will be appreciated that the transport and conveyance of the glass can be achieved by using known techniques such as roller air-float conveyors, positioners, and robotic arms, in order to handle the glass in the manner described.

Figure 8:
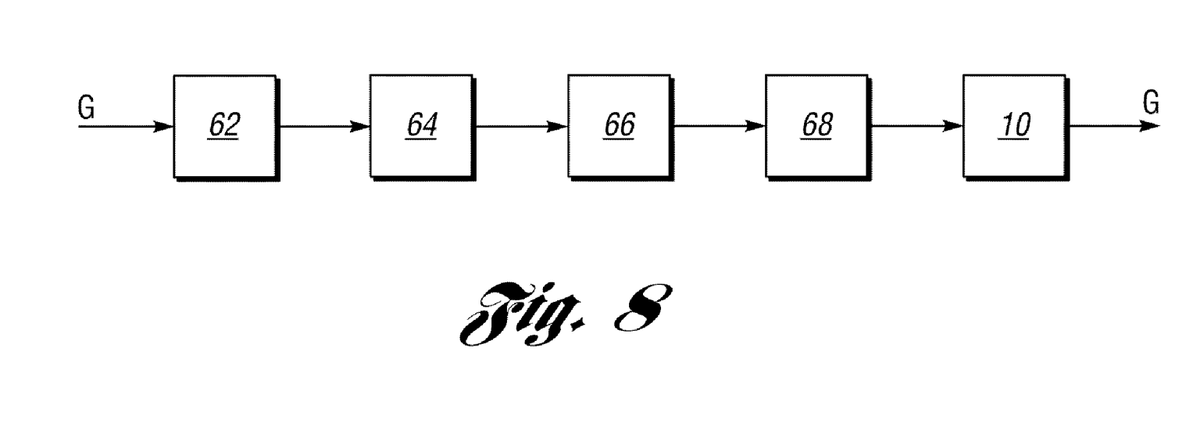
FIG. 8 is a schematic diagram of the system of the present invention installed in-line in a typical automotive windshield forming and tempering line.

FIG. 8 similarly schematically illustrates an in-line installation of the system 10 of the present invention in a typical windshield fabrication system, which may include a heating station 62, a bending station 64, a cooling station 66, and a lamination station 68, upstream of the measuring system 10. It will be appreciated that the measuring system 10 of the present invention could alternatively be mounted in-line at various other points in glass sheet fabrication systems as desired to maximize the production rate of the system, so long as the optical distortion measurements are taken after the glass sheet has been formed to its final shape.

In one embodiment the distortion indicia is formatted and stored in Microsoft Excel® format for ease of further review and manipulation by the user.

While embodiments of the present invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for measuring optical distortion in a glass sheet including:
    a digital camera,
    a background screen including a matrix of spaced apart dots positioned on a contrasting background,
    a glass stand for receiving and maintaining the glass sheet in the path between the camera and the background screen,
    at least one light source mounted in a position to illuminate the surface of the glass sheet so that the camera captures an image of the surface of the glass sheet when the glass sheet surface is illuminated,
    at least one light source mounted in a position to illuminate the background screen so that the camera captures an image of the matrix transmitted through the glass sheet, and
    a computer including logic for receiving the captured image data and (1) analyzing at least the surface image data to determine whether there are any surface marks or elements on the glass sheet that should not be considered in the optical distortion analysis, (2) locating and isolating the data corresponding to any such surface marks or elements in the image of the matrix, and (3) determining a magnification and lens power associated with each point of interest on the matrix without considering the isolated data.

2. In a system for fabricating glass sheets including a heating station for heating the glass sheet to a temperature adequate to soften the glass for forming into a desired shape, a bending station wherein the softened sheet is formed to the desired shape, a cooling station wherein the formed glass sheet is cooled in a controlled manner, and one or more conveyors for conveying the glass sheet from station to station during processing, an apparatus for measuring optical distortion in the glass sheet including:
    a digital camera;
    a background screen including a matrix of spaced apart dots positioned on a contrasting background,
    a glass stand for receiving and maintaining the glass sheet in the path between the camera and the background screen,
    at least one light source mounted in a position to illuminate the surface of the glass sheet so that the camera captures an image of the surface of the glass sheet when the glass sheet surface is illuminated,
    at least one light source mounted in a position to illuminate the background screen so that the camera captures an image of the matrix transmitted through the glass sheet, and
    a computer including logic for receiving the captured image data and (1) analyzing at least the surface image data to determine whether there are any surface marks or elements on the glass sheet that should not be considered in the optical distortion analysis, (2) locating and isolating the data corresponding to any such surface marks or elements in the image of the matrix, and (3) determining a magnification and lens power associated with each point of interest on the matrix without considering the isolated data.

* * * * *